(12) United States Patent
Bouhraoua et al.

(10) Patent No.: US 8,544,646 B2
(45) Date of Patent: Oct. 1, 2013

(54) MEDICAL SAFETY BOX

(75) Inventors: Abdelhafid Bouhraoua, Dhahran (SA); Malick Ndiaye, Dhahran (SA); Merah Farouk, Dhahran (SA); Ahmad Hamoud Ahmad Dehwah, Dhahran (SA); Saad Addin Almourad, Jeddah (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 319 days.

(21) Appl. No.: 13/154,354

(22) Filed: Jun. 6, 2011

(65) Prior Publication Data

US 2012/0305428 A1 Dec. 6, 2012

(51) Int. Cl.
*A61B 17/06* (2006.01)
*G06F 19/00* (2011.01)
*G08B 13/14* (2006.01)
*G06Q 10/00* (2012.01)
*G06Q 50/00* (2012.01)

(52) U.S. Cl.
USPC ............ 206/438; 235/385; 340/572.1; 705/2; 705/3

(58) Field of Classification Search
USPC ...... 206/438; 235/385; 340/572.1; 705/2–3
See application file for complete search history.

(56) References Cited

U.S. PATENT DOCUMENTS

| | | | |
|---|---|---|---|
| 4,763,810 A | 8/1988 | Christiansen | |
| 5,014,875 A | 5/1991 | McLaughlin et al. | |
| 5,694,919 A | 12/1997 | Rubsamen et al. | |
| 6,169,707 B1 | 1/2001 | Newland | |
| 7,191,777 B2 | 3/2007 | Brand et al. | |
| 8,240,565 B2 * | 8/2012 | Iizuka | 235/385 |
| 2003/0052787 A1 * | 3/2003 | Zerhusen et al. | 340/573.1 |
| 2008/0129496 A1 * | 6/2008 | Koblasz | 340/540 |
| 2009/0043253 A1 | 2/2009 | Podaima | |
| 2009/0182582 A1 * | 7/2009 | Hammon | 705/3 |
| 2009/0236954 A1 | 9/2009 | Kobayashi et al. | |
| 2009/0243833 A1 | 10/2009 | Huang et al. | |
| 2009/0259336 A1 * | 10/2009 | Ratnakar | 700/236 |
| 2009/0276090 A1 | 11/2009 | Rajiv | |
| 2009/0301925 A1 | 12/2009 | Alloro et al. | |

FOREIGN PATENT DOCUMENTS

WO WO2006122167 A3 1/2007
WO WO2009158037 A1 12/2009

* cited by examiner

*Primary Examiner* — Joseph Burgess
(74) *Attorney, Agent, or Firm* — Richard C. Litman

(57) ABSTRACT

The medical safety box is a system using RFID (Radio Frequency Identification) technology to ensure that correct delivery of the correct treatment in the form of medication or injection to in-hospital patients is consistently carried out. The system includes a medical box containing whatever medication or injection that needs to be administered to a specific patient. The box has a locking mechanism that can only be opened by an RFID wristband, which is worn by that same specific patient, thus assuring that the medicine in the box is administered to the correct patient.

11 Claims, 4 Drawing Sheets

MEDICAL SAFETY BOX

BACKGROUND OF THE INVENTION

1. Field of the Invention

The present invention relates to medicine dispensing systems, and particularly to a medical safety box.

2. Description of the Related Art

An important healthcare issue is clinical errors in medication administration that sometimes occur in hospitals and clinics. Nurses, who are often in charge of supplying the inpatients with their prescribed medications, injections, or simple operations, are often subject to mistakes, confusing one patient with another. Many errors and mistakes can occur, and wrongful administration could cause disastrous consequences to those patients, leading to worsening of illness and, in the worst case scenario, death. These mistakes can occur due to the fact that nurses that administer these drugs might be too relaxed and take their duty too easily, which can cause mix-ups of drugs. A solution to deal with this problem is to limit access to these drugs in such a way that specific drugs are given to the respective patient.

Thus, a medical safety box solving the aforementioned problems is desired.

SUMMARY OF THE INVENTION

The medical safety box is a system using RFID (Radio Frequency Identification) technology to ensure that correct delivery of the correct treatment in the form of medication or injection to in-hospital patients is consistently carried out. The system includes a medical box containing whatever medication or injection that needs to be administered to a specific patient. The box has a locking mechanism that can only be opened by an RFID wristband, which is worn by that same specific patient, thus assuring that the medicine in the box is administered to the correct patient.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
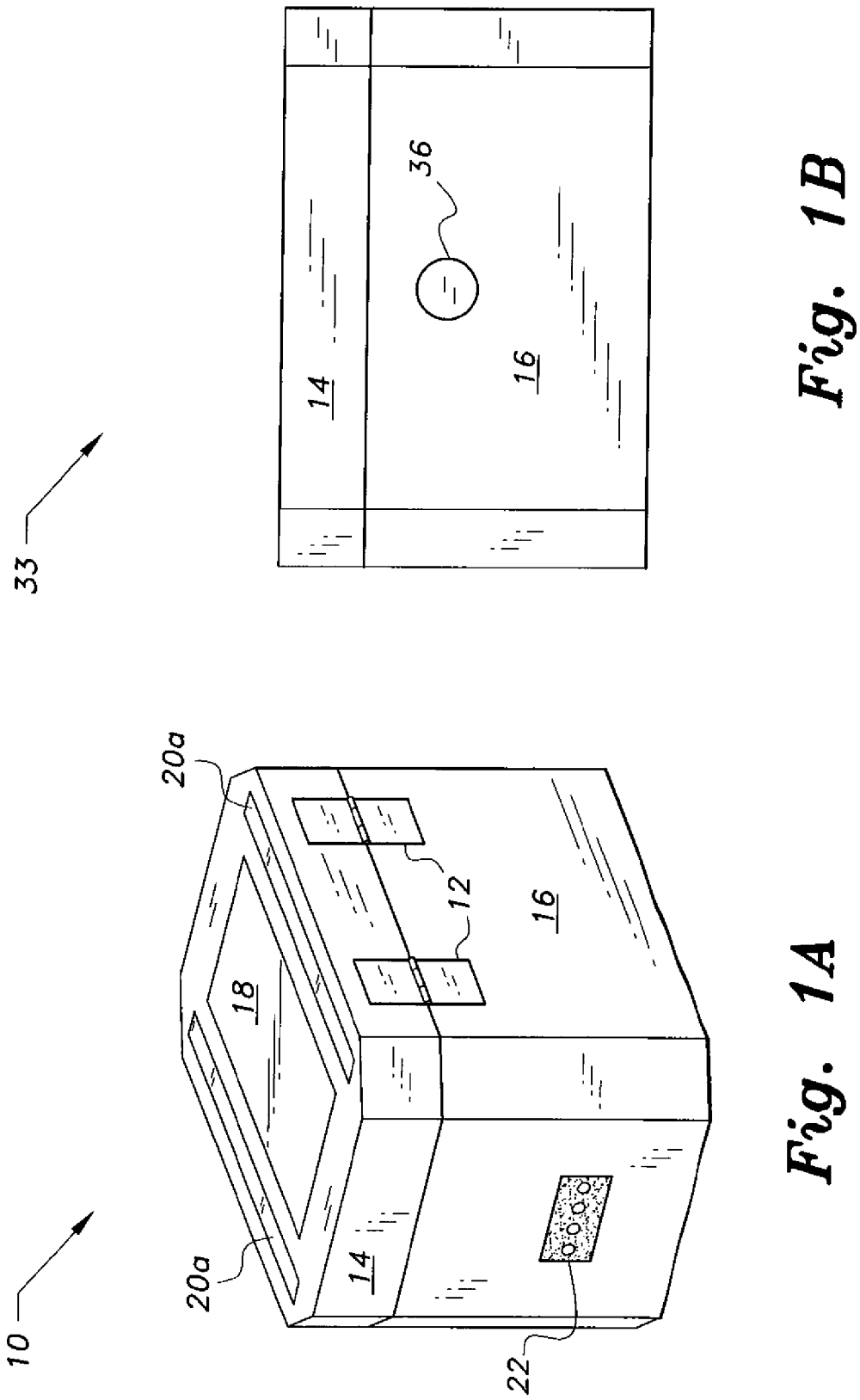
FIG. 1A is a perspective view of a medical safety box according to the present invention.
FIG. 1B is a front view of the medical safety box of FIG. 1.

As shown in FIGS. 1A through 4, the medical safety box 10 is included in a system using RFID (Radio Frequency Identification) technology to ensure that correct delivery of the correct treatment in the form of medication or injection to hospital in-patients is consistently carried out. The medical box 10 can contain whatever medication or injection is needed to be administered to a specific patient. As most clearly shown in FIG. 1A, the medical box 10 has a lid 14 and hinges 12 that pivotally attach the lid 14 to the open-top container portion 16 of the box, allowing the lid 14 to be pivoted, thereby opening or shutting the container portion 16. In the open configuration, the container portion 16 of the box 10 can be filled with vials, syringes, pillboxes, and the like, which should be delivered to a specific patient. An electronically controlled opening/closing system is comprised of an RFID-controlled lock 36 (shown in FIG. 1B), which secures the lid 14 in the shut configuration once the box 10 has been loaded with medicine for the patient.

The bottom face 37 of the medical box 10 has an RFID reader 28 that is pre-programmed to scan for a specific, unique RFID code. The subject patient wears a tag that has the specific, unique RFID code. When the box 10 is brought in proximity of the patient having the correct RFID tag, the RFID reader 28 responds by sending a signal to the lock 36, which allows the lid 14 to be opened. The caregiver can then retrieve the contents of the box 10 to administer patient-specific medicine to the patient having the proper RFID code. The box 10 is configured automatically by its computer system and the hospital ERP (Enterprise Resource Planning) system. The hospital's ERP computer system can program and track multiple devices 10. Information, such as patient name and identification, prescribing practitioner, department or hospital section, prescription information, time of issue, and any supplemental information that might be of use, is entered into the system. The details of an exemplary computer system of the type used in connection with the present invention are described and disclosed within U.S. patent application No. 2009/0043253, published on Feb. 12, 2009, entitled "Smart Medical Compliance Method and System," which is hereby incorporated by reference in its entirety.

Figure 2:
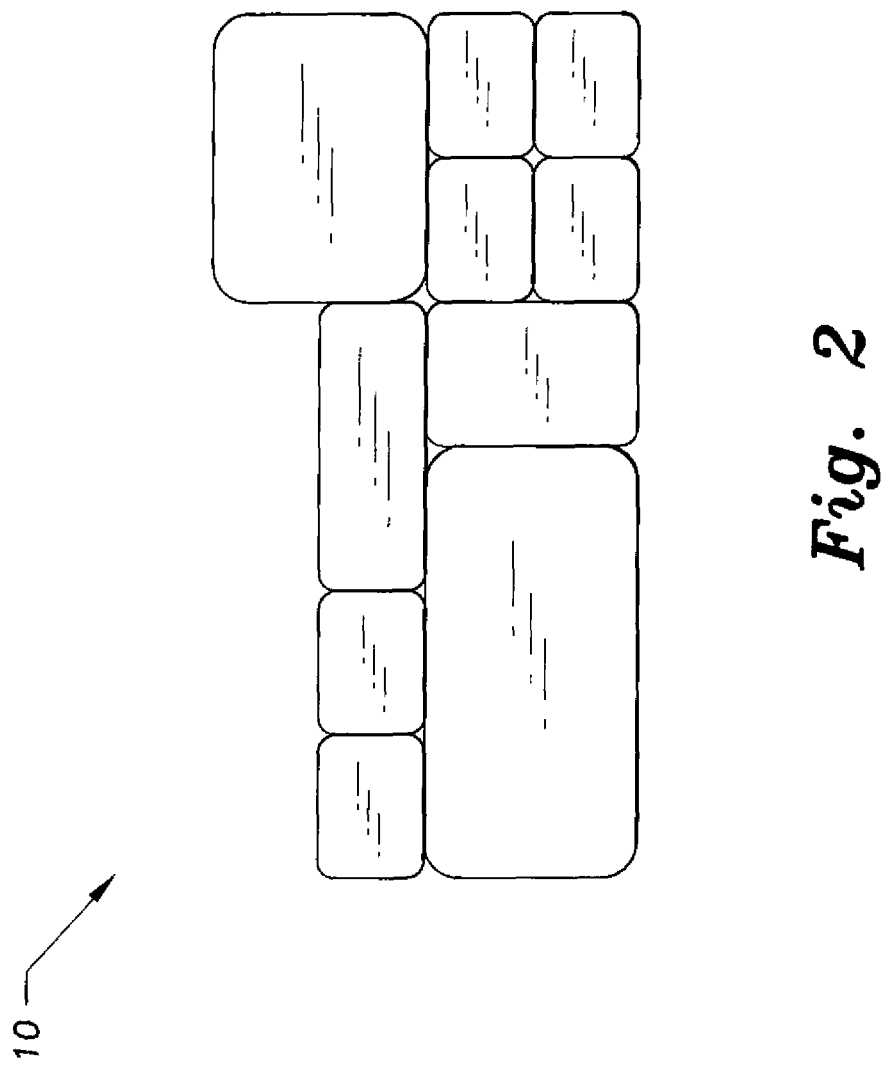
FIG. 2 is a side view of a plurality of medical safety boxes according to the present invention, showing how multiple medical safety boxes can be stacked for storage until needed.
Figure 3:
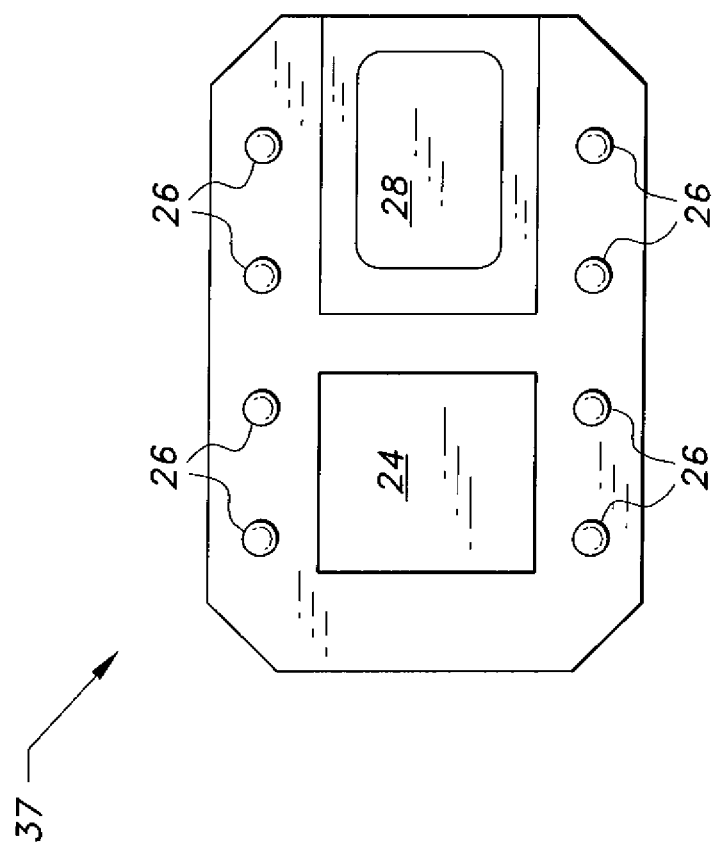
FIG. 3 is a bottom view of the medical safety box of FIG. 1.
Figure 4:
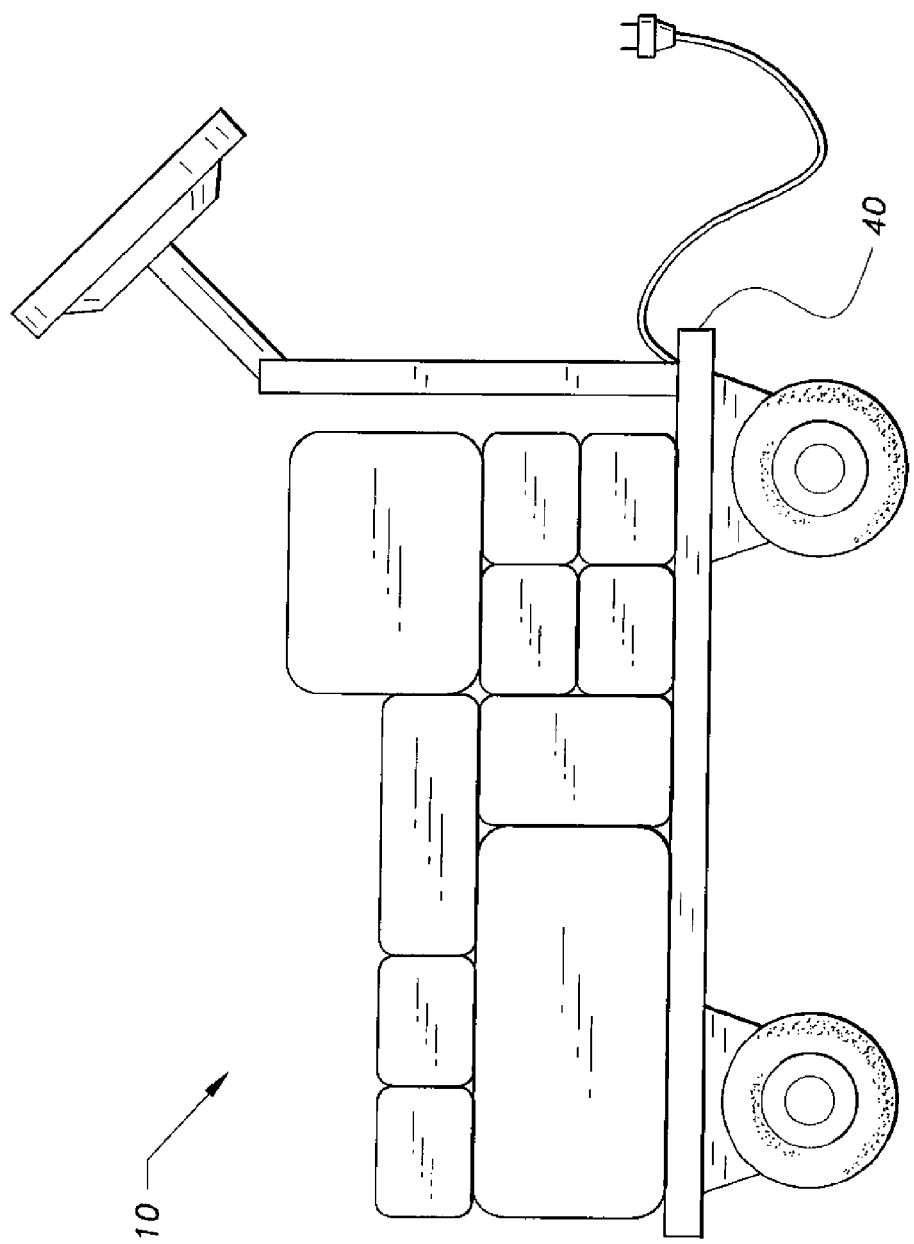
FIG. 4 is a side view of a plurality of medical safety boxes according to the present invention stacked on a power-charging tray.

The structure of the medical box 10 includes a computer interface connector 22 on its side, and combined power and signal metal strip connectors 20a on the top of lid 14. The lid also includes an LCD display 18. As shown in FIG. 2, a plurality of medical safety boxes 10 can be stacked on top of each other. The combined power and signal ball bearing connectors 26 (shown in FIG. 3) are connected to the combined power and signal metal connectors 20a, allowing the medical boxes 10 to be electrically interconnected for charging and programming purposes when they are stacked on top of a smart cart 40, as shown in FIG. 4. The control of the boxes 10 occurs through the power/signal terminals using one of the boxes at the top of the stack. One mode of operation will allow operators to display information related to a box 10 that is stacked under several layers of boxes 10. The box 10 is selected through an intuitive user interface that is displayed in a hierarchical tree, where the root of the tree is the top box and the different nodes are the layers. A simple discovery protocol can be implemented to build the tree every time access is needed. On the bottom side 37, the decision to make the connectors in the form of balls 26 has been specifically selected because of possible stacking over multiple boxes simultaneously. This makes the identification of the number and type of the boxes in the bottom much easier than if strips are used. The box 10 is configured by the hospital pharmacy at the time the prescription is processed. Medications destined for the same patient are put in the same box 10.

The medical box 10 has computer memory to save relevant information regarding medication contained in the medical box 10 and regarding the patient to whom the medication should be administered. The display screen 18 allows hospital staff to inquire about the contents of medical box 10, and to be able to perform other processing duties related to the patient and the medication to be administered from the medical box 10. Via the computer interface 22, the medical box 10 can optionally be attached to an external RFID reader. Built-in battery/batteries are accessible via a battery compartment 24. Preferably the box 10 has a recharging circuit, and a built-in calendar clock accessible via the display 18.

In hospital operations, multiple medical boxes 10 are filled and closed by the pharmacist, who then sends the medical boxes 10 to the concerned section of the hospital. Nurses receive the several boxes 10, which are destined to the many patients they have in their section of the hospital. When it is time to administer the prescribed medication to its target patient, the nurse takes the medical box 10 to the patient's bed. The nurse then takes the RFID tag attached to the patient's wrist band and slides the tag onto the RFID tag reader 28 after sliding his or her own RFID tag for identification. Responsive to correct reading and verification of the nurse's ID RFID tag and the patient's RFID tag, the electronic lock 36 unlocks box 10, allowing the lid 14 to pivot open. If the patient is not the right one, the electronic lock 36 keeps the box 10 locked and an error notification is displayed on the screen 18.

As shown in FIGS. 2 and 4, medical boxes 10 can be of different sizes, depending on the size of the items that need to be placed in them. Preferably, the box sizes are specified to enable stacking of the boxes 10 above one another, even if the sizes are different. A suggested method is to select a minimum dimension for the smallest box of H×W×D where H, W and D represent the minimum Height, Width and Depth respectively. Larger size boxes will have dimensions of kH×mW×nD, where k, m and n are positive integer values. FIG. 2 shows a typical stacking configuration of boxes 10.

A set of boxes 10 organized in a stack, as depicted in FIG. 2, should be rechargeable and should be easily movable from one location to another. To do so, transportation and power tray/cart 40 is provided. The tray or cart 40 incorporates a power converter. The tray/cart 40 can be used to transport the boxes 10 as well. The tray/cart 40 includes a power cord and a power connector that can be plugged in to a standard wall power outlet. Preferably, the tray/cart 40 also has a power supply to convert the AC power into the required DC voltage necessary to charge the batteries. Tray/cart 40 includes an information panel that is used to display the patient information and box status of the different boxes being carried.

It is to be understood that the present invention is not limited to the embodiments described above, but encompasses any and all embodiments within the scope of the following claims.

We claim:

1. A medical safety box, comprising:
 a container having an open top and a bottom, the container being adapted for containing medication to be administered to a specific patient;
 a lid pivotally attached to the container;
 a plurality of combined power-signal metal strip connectors disposed on the top of the lid;
 a plurality of combined power-signal metal ball bearing connectors disposed on the bottom of the container, the combined power-signal metal ball bearing connectors being connected in a common circuit with the plurality of combined power-signal metal strip connectors;
 an information display disposed on the top of the lid comprising means for graphically displaying a hierarchical tree structure on said information display, the hierarchical tree structure identifying information related to each of a plurality of medical safety boxes stacked on top of each other, where a displayed root of the hierarchical tree identifies a top box and different nodes of the hierarchical tree displayed below the root identify boxes below the top box;
 an electronically controlled lock releasably locking the lid closed over the open top of the container to selectively preclude access to the medication;
 an RFID tag reader electronically connected to the electronically controlled lock;
 means for programming the RFID tag reader to accept a unique RFID tag identifier number; and
 means for sending an electronic signal to open the electronically controlled lock when the RFID tag reader has read the unique RFID tag identifier number from an RFID tag attached to a patient, thereby identifying the patient as being the specific patient associated with the medication to be administered.

2. The medical safety box according to claim 1, further comprising means for displaying data about the specific patient on said information display.

3. The medical safety box according to claim 1, further comprising means for displaying data about the medications to be administered on said information display.

4. The medical safety box according to claim 1, further comprising means for displaying an error message on said information display when said unique RFID identifier number does not match an RFID identifier number read in from the patient.

5. The medical safety box according to claim 1, further comprising means for programming said medical safety box using an Enterprise Resource Planning system in a hospital setting.

6. The medical safety box according to claim 1, further comprising means for electrically charging an on-board power source utilizing said combined power-signal strip and ball bearing connectors.

7. The medical safety box according to claim 1, further comprising a computer interface connector disposed on said medical safety box.

8. The medical safety box according to claim 1, further comprising a charging cart for carrying and charging a plurality of the medical safety boxes, the charging cart including an information panel for displaying patient information and status of the medical safety boxes.

9. The medical safety box according to claim 1, further comprising means for authenticating a person administering the medication to be administered to the specific patient.

10. The medical safety box according to claim 1, further comprising a built-in calendar clock accessible via said information display.

11. The medical safety box according to claim 1, further comprising means for building said hierarchical tree structure every time access to any of the medical safety boxes is needed.

* * * * *